US012778472B2

(12) United States Patent
Burkholz et al.

(10) Patent No.: US 12,778,472 B2
(45) Date of Patent: Nov. 3, 2026

(54) EXTENSION SET FOR IMPROVING PATENCY OF A VASCULAR ACCESS DEVICE

(71) Applicant: Becton, Dickinson and Company, Franklin Lakes, NJ (US)

(72) Inventors: Jonathan Karl Burkholz, Salt Lake City, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 783 days.

(21) Appl. No.: 17/127,660

(22) Filed: Dec. 18, 2020

(65) Prior Publication Data

US 2021/0212618 A1 Jul. 15, 2021

Related U.S. Application Data

(60) Provisional application No. 62/959,068, filed on Jan. 9, 2020.

(51) Int. Cl.

*A61B 5/15* (2006.01)
*A61M 39/02* (2006.01)

(52) U.S. Cl.

CPC .. *A61B 5/150267* (2013.01); *A61B 5/150633* (2013.01); *A61M 39/0247* (2013.01);
(Continued)

(58) Field of Classification Search

CPC .... A61B 5/150732; A61B 2017/22094; A61B 5/150267; A61B 5/150633; A61B 5/15003; A61B 5/150992; A61B 5/154; A61B 5/150206; A61B 5/153; A61B 5/1535; A61B 5/1545; A61B 2017/00778; A61M 39/0247; A61M 2039/0202; A61M 2039/0205; A61M 2039/0258; A61M 2039/0276; A61M 25/0097;
(Continued)

(56) References Cited

U.S. PATENT DOCUMENTS 5,695,474 A 12/1997 Daugherty
8,366,685 B2 * 2/2013 Devgon ........... A61B 5/150511 604/173

(Continued)

FOREIGN PATENT DOCUMENTS

EP 0657140 * 6/1995
EP 2701602 3/2014

(Continued)

*Primary Examiner* — Jennifer Robertson
*Assistant Examiner* — Huong Q. Nguyen
(74) *Attorney, Agent, or Firm* — The Webb Law Firm

(57) ABSTRACT

An extension set is configured to improve patency of a vascular access device. An extension set may include a probe that can be selectively advanced through a vascular access device to which the extension set is connected. The extension set may include an integrated device, or may be configured to receive a device, for collecting blood from or injecting a fluid into a patient's vasculature. Because the probe can be selectively advanced into the patient's vasculature, a blood collection or fluid injection can be performed via the vascular access device even when an occlusion has formed that is blocking the fluid pathway through the vascular access device.

19 Claims, 8 Drawing Sheets

(52) U.S. Cl.
CPC ............... *A61M 2039/0202* (2013.01); *A61M 2039/0205* (2013.01); *A61M 2039/0258* (2013.01); *A61M 2039/0276* (2013.01)

(58) Field of Classification Search
CPC .......... A61M 25/0017; A61M 25/0113; A61M 2025/0019; A61M 25/09; A61M 25/0606; A61M 25/09041; A61M 25/0905; A61M 2025/09083; A61M 2025/09116; A61M 39/10–14; A61M 2039/1005–1094; A61M 2005/16863
See application file for complete search history.

(56) References Cited

U.S. PATENT DOCUMENTS

| | | | | |
|---|---|---|---|---|
| 9,744,344 | B1 * | 8/2017 | Devgon | A61M 39/0247 |
| 9,782,536 | B2 * | 10/2017 | Skutnik | A61M 25/007 |
| 10,064,576 | B2 | 9/2018 | Devgon | |
| 12,491,342 | B2 * | 12/2025 | Burkholz | A61M 25/0113 |
| 2004/0167385 | A1 * | 8/2004 | Rioux | A61B 5/026 600/373 |
| 2007/0118165 | A1 * | 5/2007 | DeMello | A61B 17/221 606/159 |
| 2009/0182363 | A1 * | 7/2009 | Shamay | A61B 17/320725 606/159 |
| 2012/0165789 | A1 * | 6/2012 | Deckard | A61B 17/22 604/528 |
| 2012/0191010 | A1 | 7/2012 | Cabot | |
| 2012/0277627 | A1 | 11/2012 | Devgon | |
| 2014/0188003 | A1 | 7/2014 | Belson | |
| 2017/0216564 | A1 | 8/2017 | Devgon et al. | |
| 2020/0016374 | A1 * | 1/2020 | Burkholz | A61M 25/0111 |
| 2020/0170559 | A1 * | 6/2020 | Burkholz | A61M 25/09041 |
| 2020/0205845 | A1 * | 7/2020 | Yang | A61M 25/0108 |
| 2020/0316346 | A1 * | 10/2020 | Burkholz | A61M 25/09041 |

FOREIGN PATENT DOCUMENTS

| | | | |
|---|---|---|---|
| JP | 2006511271 | A | 4/2006 |
| JP | 2017532985 | A | 11/2017 |
| JP | 2019509781 | A | 4/2019 |
| WO | 2011/011436 | | 1/2011 |

* cited by examiner

EXTENSION SET FOR IMPROVING PATENCY OF A VASCULAR ACCESS DEVICE

RELATED APPLICATIONS

This application claims the benefit of U.S. Provisional Application No. 62/959,068, filed Jan. 9, 2020, and entitled EXTENSION SET FOR IMPROVING PATENCY OF A VASCULAR ACCESS DEVICE, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into the vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is required, an additional needle stick is needed to provide vein access for blood collection, which may be painful for the patient and result in higher material costs.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to an extension set for improving or facilitating patency of a vascular access device as well as related systems and methods. An extension set may include a probe that can be selectively advanced through a vascular access device to which the extension set is connected. The extension set may include an integrated device, or may be configured to receive a device, for collecting blood from or injecting a fluid into a patient's vasculature. Because the probe can be selectively advanced into the patient's vasculature, a blood collection or fluid injection can be performed via the vascular access device even when an occlusion has formed that is blocking the fluid pathway through the vascular access device.

In example embodiments, an extension set may include one or more of the following: a distal connector; an extension tube coupled to the distal connector; a fluid pathway being formed through the distal connector and the extension tube; a probe having a proximal end and a distal end; and a handle that slides along the extension tube to cause the distal end of the probe to be extended distally from the distal connector. The extension set may also include a sleeve that extends between the distal connector and the handle with the probe being contained within the sleeve. In such cases, the extension set could include one or more rails positioned within the sleeve, the one or more rails extending proximally from the distal connector. The extension set may also include a proximal connector that is coupled to the extension tube opposite the distal connector with the fluid pathway extending through the proximal connector. Alternatively, the extension set may include an integrated device that is coupled to the extension tube opposite the distal connector with the fluid pathway extending into the integrated device.

In any of these embodiments, the proximal end of the probe may be positioned at the distal connector and the probe may be routed through the handle. Also, in any of these embodiments, the handle may surround the extension tube. In embodiments that include a sleeve, the sleeve may be configured to compress as the handle slides towards the distal connector.

In some embodiments, the probe may include a fluid permeable distal portion. As an example, this fluid permeable distal portion may comprise a coil. In embodiments where the probe includes a coil, the coil may have a distal portion that extends distally beyond the distal end of the probe. In any of these embodiments, the probe may comprise a sensor.

In some embodiments, the distal connector may include one or more seals. The probe may extend through the one or more seals. In some embodiments, a primary seal and a secondary seal positioned proximal to the primary seal may be included in the distal connector. The secondary seal may have a distally-facing pocket that is configured to collect fluid that may remain on the surface of the probe when it is withdrawn.

In other example embodiments, an extension set may include one or more of the following: a distal connector; a proximal connector; an extension tube extending between the distal connector and the proximal connector, a fluid pathway being formed through the distal connector, the extension tube and the proximal connector; a handle that is positioned between the distal connector and the proximal connector, the handle being configured to slide along the extension tube; a sleeve that extends between the distal connector and the handle; and a probe that is interfaced with the handle such that a distal end of the probe is extended distally from the distal connector when the handle slides towards the distal connector.

In such embodiments, the probe may comprise a proximal end that is positioned at the distal connector and is routed through the handle. The sleeve may surround the extension tube and a portion of the probe that is positioned between the distal connector and the handle. The probe may include a coil that forms a fluid permeable distal portion of the probe.

In other example embodiments, a method for collecting blood is disclosed. In this method, an extension set is attached to a vascular access device that is inserted into a patient's vasculature. The extension set includes: a distal connector by which the extension set is attached to the vascular access device; an extension tube coupled to the distal connector; a vacuum tube receiver coupled to the extension tube opposite the distal connector, a fluid pathway being formed through the distal connector, the extension tube and the vacuum tube receiver; a probe having a proximal end and a distal end; and a handle that slides along the extension tube to cause the distal end of the probe to be extended distally from the distal connector. With the extension set attached to the vascular access device, a vacuum tube is inserted into the vacuum tube receiver. The handle is then moved towards the distal connector to cause the distal end of the probe to be extended through the vascular access device and into the patient's vasculature thereby removing an occlusion that is preventing blood from flowing through the fluid pathway into the vacuum tube.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

In the specification and the claims, the term "vascular access device" should be construed as any device that is configured to be inserted into an individual's vasculature to enable access for blood collection, fluid injection or other similar purposes. A peripheral intravenous catheter (PIVC) is one common example of a vascular access device. The term "extension set" should be construed as any device that can be connected to a vascular access device. In this context, the present disclosure can be viewed as encompassing various configurations of extension sets that can be used to improve the patency of a vascular access device.

Figure 1A:
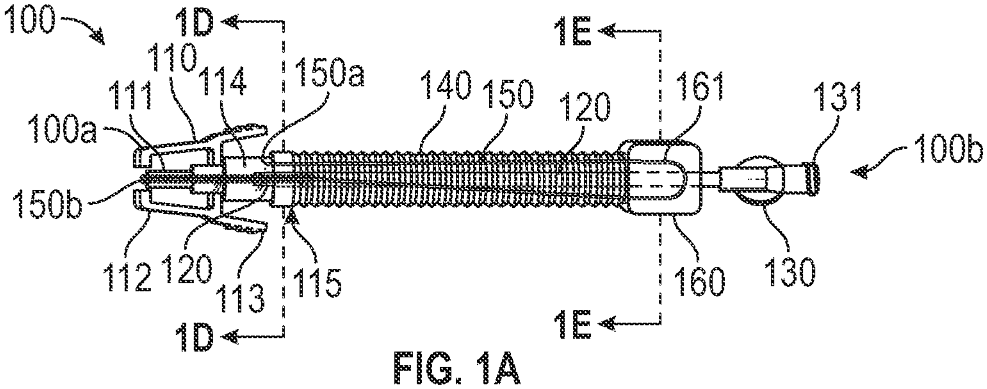
FIG. 1A illustrates an example of an extension set that is configured in accordance with some embodiments.
Figure 1B:
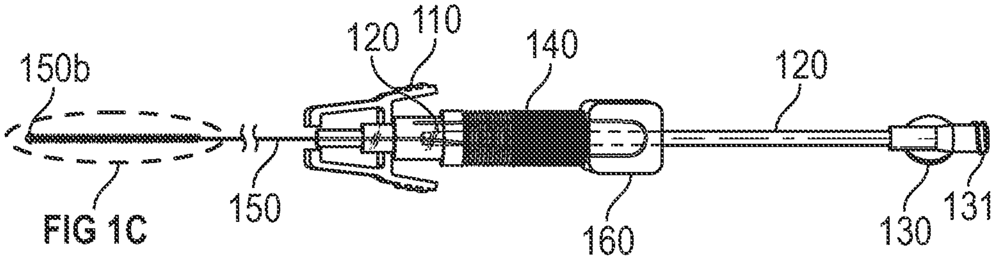
FIG. 1B illustrates the extension set with a probe extended distally from the extension set.

FIGS. 1A and 1B each illustrate an example of an extension set 100 that is configured in accordance with embodiments of the present disclosure. Extension set 100 includes a distal connector 110 at a distal end 100*a* of extension set 100, a proximal connector 130 at a proximal end 100*b* of extension set 100, an extension tube 120 that extends between distal connector 110 and proximal connector 130 and that provides a fluid pathway 121 therethrough, a collapsible sleeve 140 that surrounds extension tube 120 and has a distal end that is coupled to distal connector 110, a handle 160 that is coupled to the proximal end of collapsible sleeve 140 and a probe 150 that is primarily positioned within collapsible sleeve 140 and is configured to extend distally from distal connector 110.

Distal connector 110 can be configured in any form that would enable it to be coupled to a vascular access device (e.g., a blunt cannula snap connect, a threaded male luer, a slip luer, a threaded male luer with removably attached blunt cannula snap connect, etc). In the depicted embodiment, distal connector 110 has a cannula 111 that may be inserted into a port of the vascular access device, arms 112 positioned on opposing sides of cannula 111 that can secure distal connector 110 to the port and tabs 113 for actuating arms 112. Cannula 111 may be fluidly coupled to extension tube 120 (e.g., via a lumen of distal connector 110 into which a distal end of extension tube 120 extends). A proximal portion 114 of distal connector 110 may house one or more seals 115 to prevent the flow of fluid (e.g., blood) proximally out from distal connector 110 except through extension tube 120. As best represented in FIG. 1D, probe 150 may pass through such seal(s) 115. Proximal connector 130 may also be configured in any form that would enable another device to be connected to extension set 100. For example, proximal connector 130 may form a female luer adapter 131.

The configuration of extension tube 120 may be optimized to minimize hemolysis while providing adequate flow rate through extension set 100. For example, extension tube 120 may be configured in accordance with the techniques described in U.S. Patent Appl. No. 62/951,736 which is incorporated herein by reference.

Compressible sleeve 140 may be formed of any suitable material including, for example, a tubular polymer film, a tubular polymer film with a light coil spring, a baffled material, a collapsible elastomeric or polymer sleeve, etc. In some embodiments, compressible sleeve 140 may be formed of a semi or fully transparent material to enable the clinician to view probe 150 during use. Handle 160 may also be formed of a semi or fully transparent material.

Probe 150, which may be in the form of a guidewire in some embodiments, includes a proximal end 150*a* that may be secured to or within proximal portion 114 of distal connector 110 and a distal end 150*b* that may initially be contained within distal connector 110 (e.g., towards the distal end of cannula 111). As represented in FIG. 1B, distal end 150*b* of probe 150 may be extended from cannula 111 to thereby cause distal end 150*b* to pass into and possibly through a vascular access device to which extension set 100 may be coupled.

As illustrated, probe 150 can be routed through handle 160 (e.g., via a channel 161) to thereby cause probe 150 to extend distally when handle 160 is moved distally towards distal connector 110 (e.g., as handle 160 is slid along extension tube 120). For example, handle 160 may include a channel within which probe 150 slides as the distal movement of handle 160 feeds probe 150 out from cannula 111. This channel may be lubricated or otherwise configured to minimize friction on probe 150.

Figure 1C:
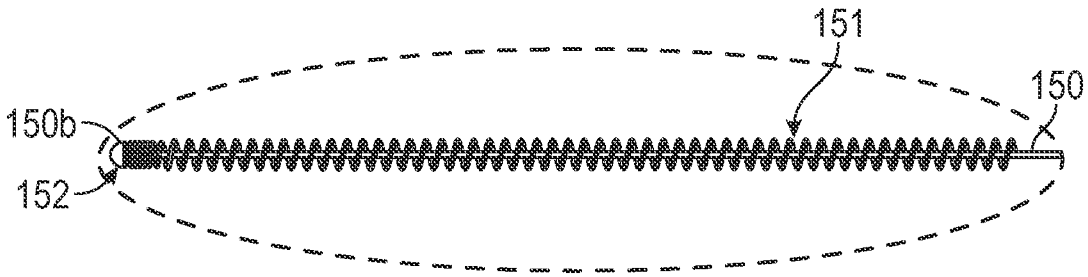
FIG. 1C illustrates a distal portion of the probe.
Figure 1D:
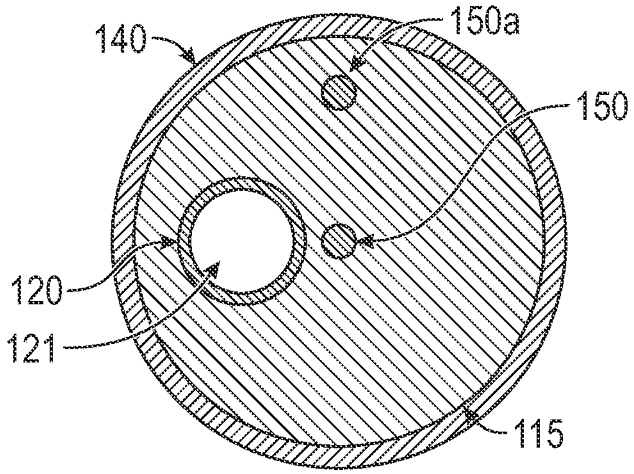
FIG. 1D provides a cross-section through the distal connector of the extension set.
Figure 1E:
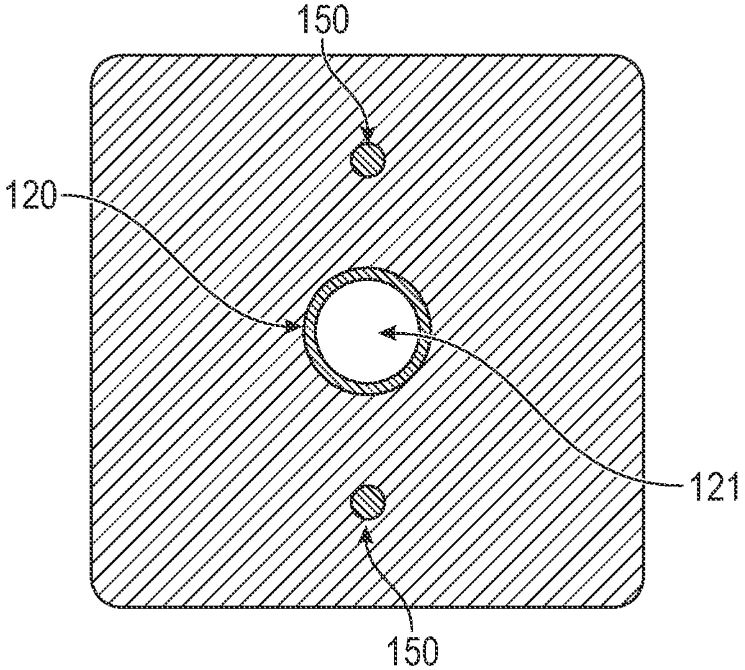
FIG. 1E provides a cross-section through the handle of the extension set.
Figure 1F:
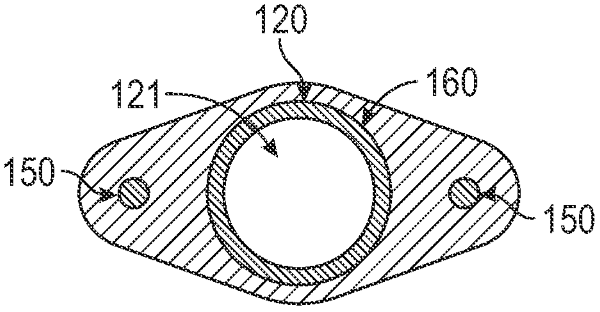
FIGS. 1F-1I provide cross-sections of other handle configurations that can be employed on the extension set.
Figure 1G:
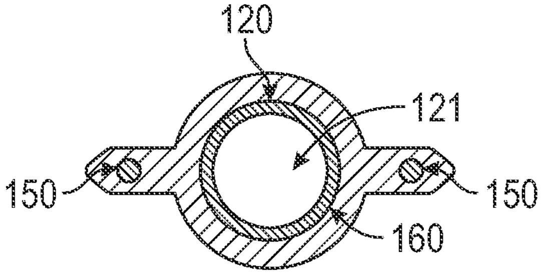
Figure 1H:
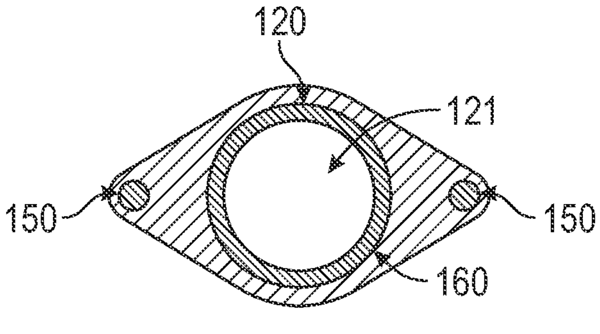
Figure 1I:
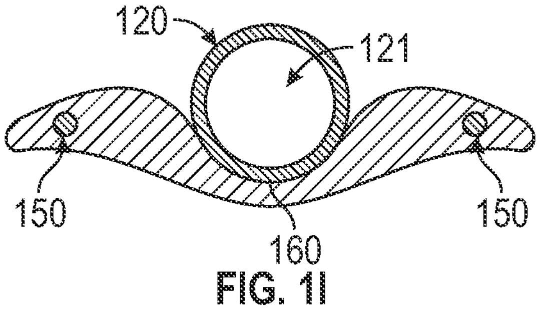

FIG. 1E provides a cross-section through handle 160 illustrating how probe 150 and extension tube 120 may extend therethrough. FIGS. 1F-1I each illustrate a variation of handle 160 that can be used in embodiments of an extension set including extension set 100. As illustrated, in some embodiments, handle 160 need not surround extension tube 120. In the embodiments depicted in FIGS. 1F-1I, although the sleeve is not illustrated, it may be configured to match the cross-sectional shape of handle 160 to thereby contain probe 150 and possibly extension tube 120.

Because probe 150 is doubled back on itself (or more particularly, because probe 150 extends proximally from proximal end 150*a* to pass through handle 160 and then returns distally), there will be a 2:1 ratio between the distance that probe 150 is extended and the distance that handle 160 is moved. This enables the length of extension set 100 to be reduced. It is noted, however, that distal end 150*a* could be secured to handle 160 to provide a 1:1 ratio (i.e., probe 150 need not be doubled back). Similarly, a 3:1 ratio could be obtained by securing distal end 150*a* to handle 160, then routing probe 150 through a channel in distal connector 110 followed by routing probe 150 through a channel in handle 160.

In an example use case, a clinician may connect extension set 100 to a vascular access device when extension set 100 is in the position illustrated in FIG. 1A. Then, the clinician can grip handle 160 and slide it towards distal connector 110 to cause probe 150 to be extended into, and typically through, the vascular access device so that distal end 150*b* is positioned within the patient's vasculature. In some embodiments, one or more markings may be formed on extension tube 120 which represent the position of distal end 150*b* of probe 150 relative to the position of handle 160. For example, the sliding of handle 160 may expose a marking that indicates when distal end 150*b* will have reached the opening of a catheter on a known vascular access device.

With probe 150 extended, extension set 100 may then be used to perform a blood collection, fluid injection or some other procedure (e.g., by connecting a blood collection set or syringe to proximal connector 130). As mentioned above, proximal portion 114 may include one or more seals 115 that are configured to allow fluid to flow between cannula 111 and extension tube 120 while preventing the proximal flow of fluid outside of extension tube 120. Subsequently, the clinician may slide handle 160 proximally to retract probe 150 into extension set 100. Probe 150 will be contained within collapsible sleeve 140 to thereby prevent exposure to blood or other fluids. In some embodiments, handle 160 may form a fluid tight seal around extension tube 120 to prevent fluid from escaping from collapsible sleeve 140 after probe 150 has been withdrawn.

As represented in FIG. 1C, in some embodiments, probe 150 may be configured with a fluid permeable distal portion. In the depicted embodiment, this fluid permeable distal end is formed using a coil 151 that extends around the distal end of probe 150 (e.g., a nitinol guidewire core). An inner surface of coil 151 may be spaced from probe 150 to thereby allow fluid to flow between probe 150 and coil 151. Accordingly, when probe 150 is extended into the vasculature through a catheter of a vascular access device, the spacing between coil 151 and probe 150 will ensure that a fluid pathway exists into the catheter even though probe 150 is extending out from the catheter. FIG. 1C also shows that, in some embodiments, distal end 150*b* of probe 150 may include a cap 152. Cap 152 may have a distally-facing rounded surface to facilitate insertion of probe 150 through a vascular access device and to minimize trauma to the vasculature. In some embodiments, cap 152 may comprise a sensor for measuring pressure, temperature, pH, blood chemistry, SPO2, flow rate, etc.

Figure 2:
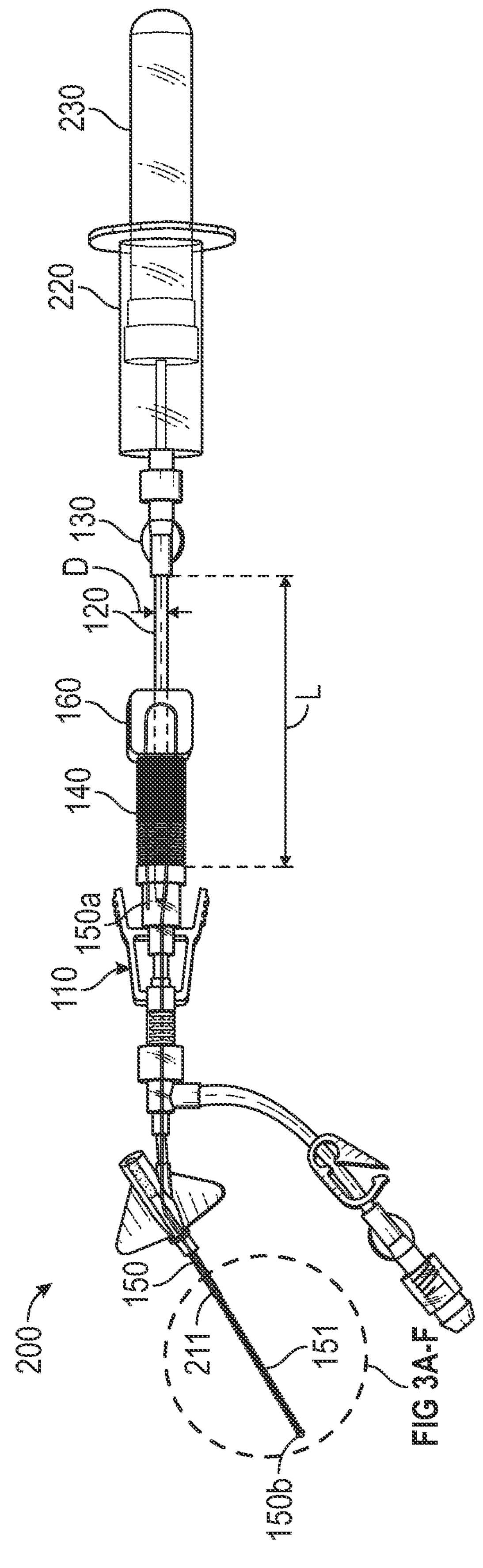
FIG. 2 illustrates how the extension set can be coupled to a vascular access device.

FIG. 2 provides an example of how extension set 100 can be connected to a PIVC 200 to enable blood to be collected using a vacuum tube adapter 220 and vacuum tube 230. PIVC 200 includes a catheter 211 that would be positioned in the vasculature when in use. As illustrated, with handle 160 slid distally, probe 150 will extend out from catheter 211 and into the vasculature. In some embodiments, the length of the fluid permeable distal portion may be configured such that a portion of coil 151 remains within catheter 211 when handle 160 is slid fully towards distal connector 110. During the dwell time of catheter 211, the opening of catheter 211 may become occluded (e.g., by fibrin material, thrombosis, the vein wall, a valve, etc.), the likelihood of which typically increases with the dwell time. In such cases, the advancing of probe 150 through catheter 211 will remove the occlusion thereby opening a fluid pathway through catheter 211 and ultimately into vacuum tube 230. In contrast, without the use of extension set 100, it is much more likely that PIVC 200 will need to be replaced due to the occlusion. The advancing of probe 150 may also open any downstream valve located anywhere in the system.

In addition to using combination of PIVC 200 and extension set 100 to collect blood, the combination could also be used to inject a fluid. For example, a syringe or other device could be connected to proximal connector 130 to thereby inject fluid into extension tube 120. Because probe 150 has been extended into the vasculature, the fluid can freely flow into the vasculature even if an occlusion had formed around catheter 211's opening.

Figure 3A:
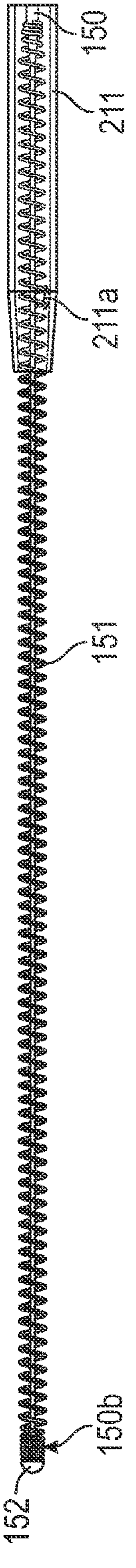
FIGS. 3A-3F illustrate various examples of how a distal portion of a probe can be configured to be fluid permeable.
Figure 3B:
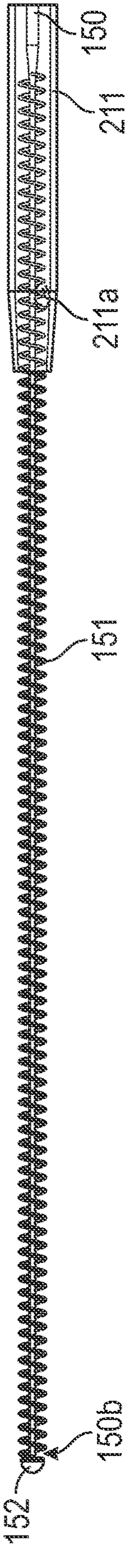
Figure 3C:
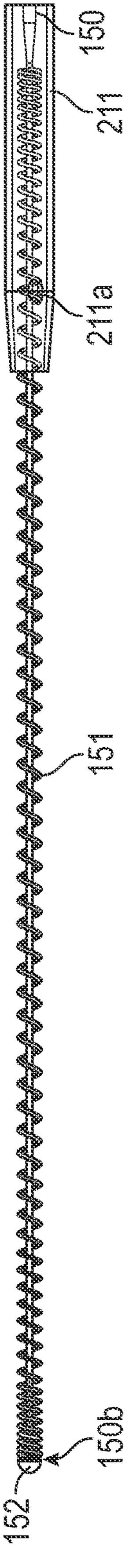
Figure 3D:
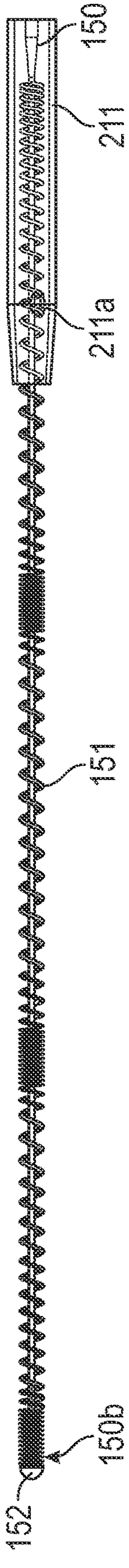
Figure 3E:
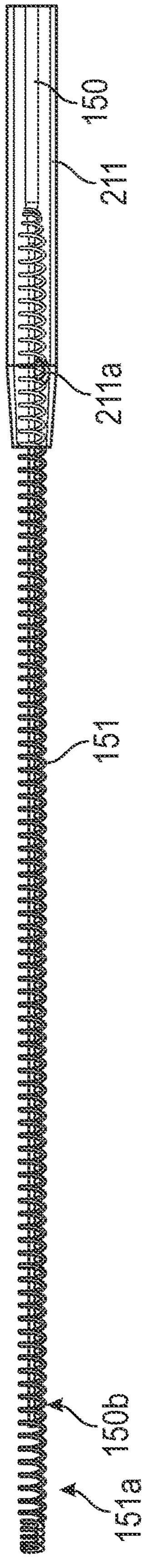
Figure 3F:
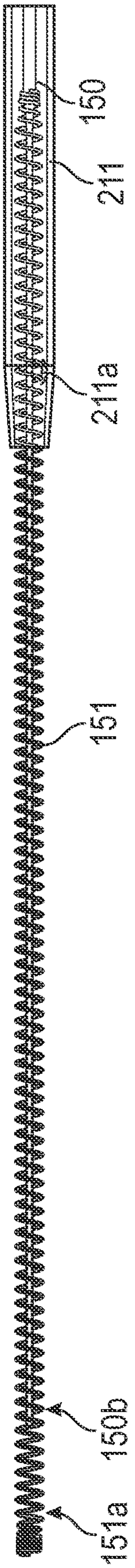

FIGS. 3A-3F illustrate various examples of how a fluid permeable distal portion can be formed on probe 150. As illustrated, coil 151 can have a constant pitch along its length (i.e., a constant spacing between the centers of adjacent coils) or a variable pitch. For example, in FIGS. 3A and 3C, the pitch of coil 151 is constant along the majority of its length but is reduced at distal end 150*b*. In FIG. 3D, coil 151 has repeating sections of reduced pitch. FIGS. 3E and 3F illustrate embodiments where coil 151 includes a distal portion 151*a* that extends beyond distal end 150*b* of probe 150. In the embodiments depicted in FIGS. 3E and 3F, probe 150 does not include cap 152, but a cap 152 could be included on coils having distal portion 151*a*. FIGS. 3A-3F also illustrate that a vascular access device designed for use with extension set 100 can include a catheter 211 having one or more sidewall openings 211*a* which provide an alternate fluid pathway into catheter 211.

Figure 4:
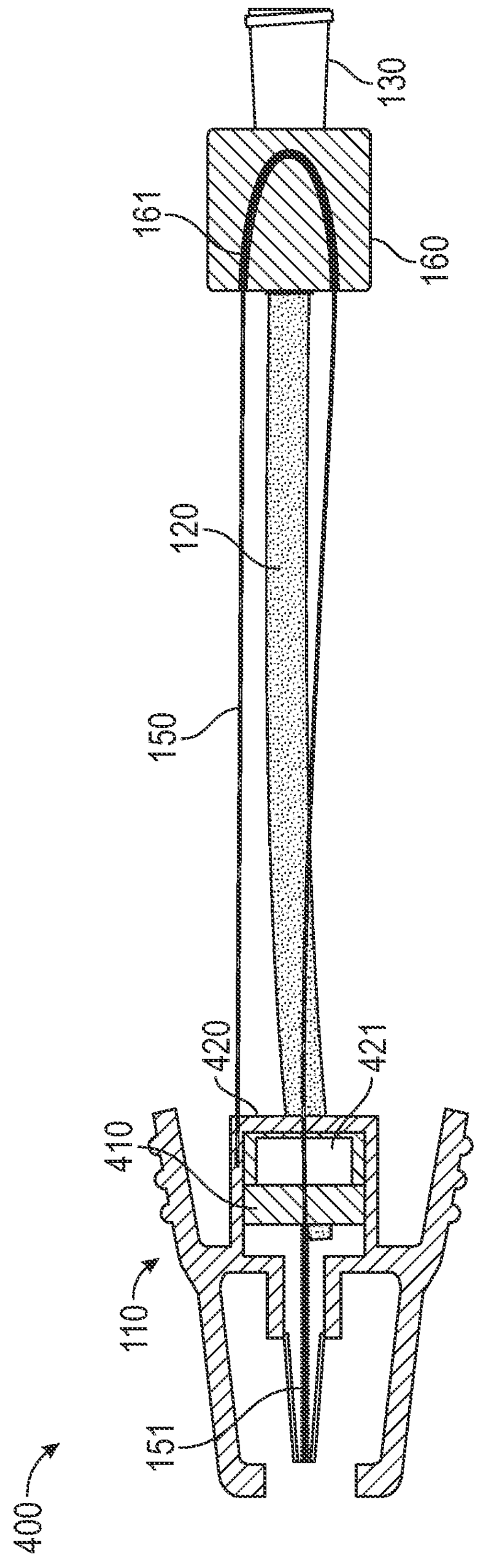
FIG. 4 illustrates another example of an extension set that is configured in accordance with some embodiments.

FIG. 4 illustrates another example of an extension set 400 that is configured in accordance with embodiments of the present disclosure. Extension set 400 is substantially similar to extension set 100 but represents a number of variations. For example, extension set 400 does not include a sleeve such that probe 150 is exposed between distal connector 110 and handle 160. In such embodiments, to prevent exposure to fluids that may exist on probe 150 after it is withdrawn, a primary seal 410 and a secondary seal 420 may be positioned within distal connector 110. Primary seal 410 may be similar to seal 115 described above. Secondary seal 420 may be positioned proximal to primary seal 410 and may include a distally-facing pocket 421. Extension tube 120 can extend through primary seal 410 and secondary seal 410. In the depicted embodiment, extension tube 120 does not extend through pocket 421. For example, pocket 421 may be formed at one side of secondary seal 420 and extension tube 120 may extend through the opposite side of secondary seal 420. In other embodiments, however, extension tube 120 could pass through pocket 421.

As probe 150 is withdrawn proximally, primary seal 410 may wipe fluid from the probe's surface. Secondary seal 420 may wipe any remaining fluid and cause it to be collected within pocket 421. Accordingly, even though a portion of probe 150 that was in contact with fluid may be retracted proximally beyond secondary seal 420, any fluid will have been removed from the surface of probe 150 to thereby minimize or eliminate the risk of contact with the fluid. Given that primary seal 410 and secondary seal 420 prevent fluid from passing proximally out from distal connector 110 except through extension tube 120, handle 160 need not provide any form of seal around extension tube 120 in such embodiments.

Figure 5:
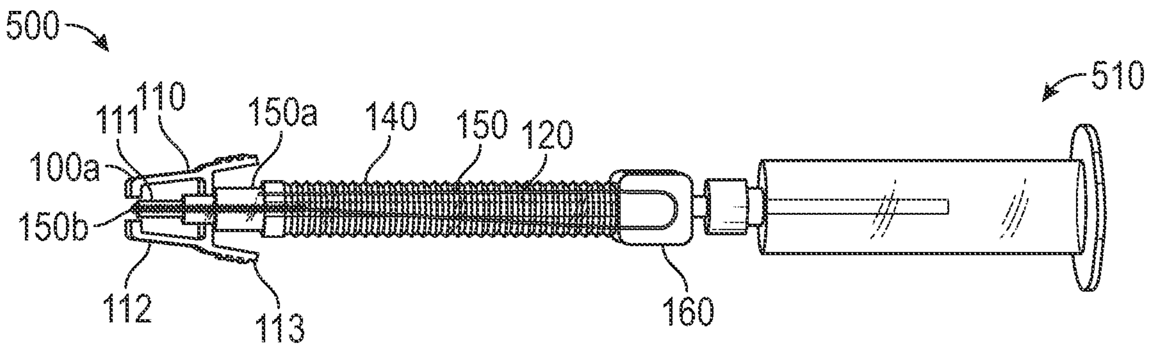
FIG. 5 illustrates another example of an extension set that is configured in accordance with some embodiments.

FIG. 5 illustrates another example of an extension set 500 that is similar to extension set 100 but includes an integrated device 510 as opposed to proximal connector 130. In this case, integrated device 510 is a vacuum tube adapter, but other integrated devices could be used.

Figure 6A:
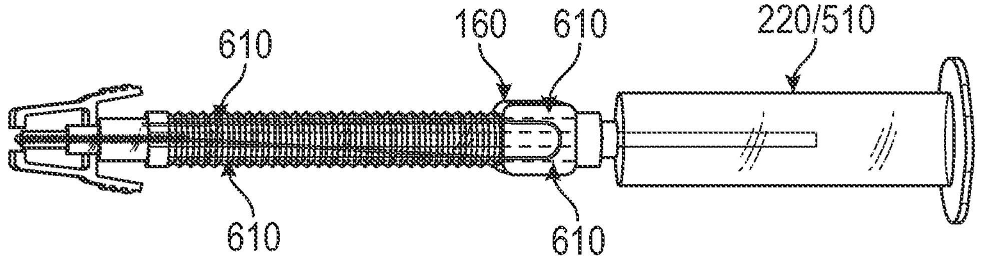
FIGS. 6A and 6B illustrate another example of an extension set that is configured in accordance with some embodiments.
Figure 6B:
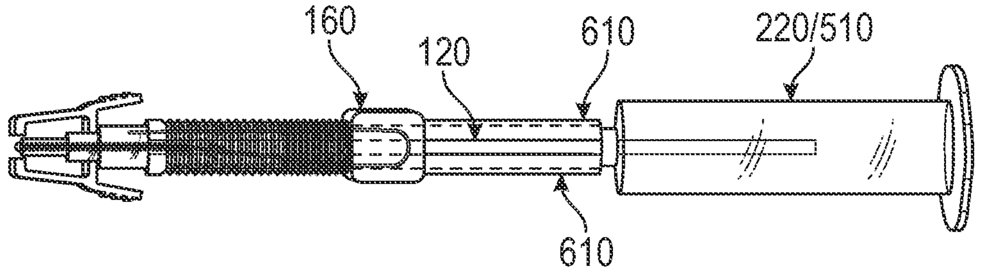

FIGS. 6A and 6B illustrate another example of an extension set 600 that is similar to extension sets 100 and 500 but includes rails 610 which extend proximally from distal connector 110 and are positioned within sleeve 140. In the depicted embodiment, rails 610 also connect to the distal end of integrated device 510. Rails 610 can function to reinforce extension set 600 and may also function as guides for sliding handle 160. In embodiments that do not include integrated device 510, rails 610 could connect to proximal connector 130. In other embodiments, however, the proximal end of rails 610 may be spaced from and not connected to integrated device 510 or proximal connector 130. For example, the proximal ends of rails 610 could be positioned within handle 160 when handle 160 is in its proximal-most position.

In some embodiments, an extension set that includes an integrated or pre-attached vacuum tube receiver (e.g., as illustrated in FIGS. 2, 5 and 6) may be used to perform a unique method for collecting blood. For example, a clinician can connect extension set 100 with vacuum tube receiver 220 pre-attached to PIVC 200. Then, the clinician can insert vacuum tube 230 into vacuum tube 220. If blood is flowing, the clinician can proceed to collect blood into vacuum tube(s) 230. However, if blood is not flowing or stops flowing at any point, the clinician can slide handle 160 distally to extend probe 150 into the patient's vasculature to remove any occlusion and then complete the collection. Once the blood is collected, the clinician may slide handle 160 to withdraw probe 150 and then remove extension set 100 from PIVC 200.

In some embodiments, a length of the extension tube 120 may be selected based on one or more of the following: a gauge and/or length of a particular PIVC 200, a particular catheter assembly configuration, or a clinical setup. In some embodiments, the extension tube 120 may include a length L from a distal end of the extension tube 120 and the proximal connector 130 (see, for example, FIG. 2). In some embodiments, the extension tube 120 may include an inner diameter D.

Fluid flow in an extension tube with a tubular fluid pathway therethrough, such as the extension tube 120, for example, can be analyzed using Poiseuille's equation:

$$Q = \frac{\pi D^4 \Delta P}{128\ \mu L} = \frac{\Delta P}{R_f}$$

where ΔP is a change in pressure gradient across the length of the extension tube, D and L are the inner diameter and length, respectively, of the tubular fluid pathway through the extension tube, μ is the viscosity of a fluid, and $$R_f = \frac{128\ \mu L}{\pi D^4}$$

is the fluid resistance. Since μ is the viscosity of the fluid and not part of the extension tube geometry, a geometric factor $G_f$ is defined such that $R_f$ (the fluid resistance) is $$R_f = \frac{128\ \mu}{\pi} G_f,$$

where $$G_f = \frac{L}{D^4}.$$

In some embodiments, the extension tube 120 may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the extension tube 120 may have an inner diameter that changes over the length of a lumen of the extension tube 120, the geometric factor is then:

$$G_f = \int_0^L \frac{dl}{D(l)^4}$$

In some embodiments, the extension tube 120 may have a cross section that is not circular. In this case, the geometric factor can be determined by measuring the flow rate (Q) at given pressure (ΔP) with known viscosity (μ) fluid:

$$G_f = \frac{\pi \Delta P}{128\ \mu Q}$$

The $G_f$ value may be selected to reduce the max shear stress for each IV device gauge to be the same or less than the max shear stress of a BD 21G VACUTAINER® UTLRATOUCH™ push button blood collection set (available from Becton Dickinson & Company of Franklin Lakes, New Jersey), which was previously considered the gold standard for blood draws. In some embodiments, $G_f$ may be equal to or more than 3.83E+06 (1/in$^3$) when the PIVC includes a 18G catheter, which may reduce the wall sheer stress to reduce hemolysis. In some embodiments, $G_f$ may be equal to or more than 3.27E+06 (1/in$^3$) when the PIVC includes a 20G catheter, which may reduce the wall sheer stress to reduce hemolysis. In some embodiments, $G_f$ may be equal to or more than 3.33E+06 (1/in$^3$) when the PIVC is a 22G catheter, which may reduce the wall sheer stress to reduce hemolysis. In some embodiments, $G_f$ may be equal to or more than 1.50E+07 (1/in$^3$) when the PIVC includes a 24G catheter, which may reduce the wall sheer stress to reduce hemolysis. In some embodiments, $G_f$ may include another value. In some embodiments, $G_f$ value may be selected to reduce the max shear stress for each catheter gauge to be the same or less than the max shear stress of a BD 25G VACUTAINER® ULTRATOUCH™ push button blood collection set (available from Becton Dickinson & Company of Franklin Lakes, New Jersey).

In some embodiments, a fluid pathway of a blood collection system, which may include one or more of the vacuum tube adapter 220, the extension tube 120, and the PIVC 200 (which may include an extension tube), may include an entirety of a blood collection pathway through which blood flows during blood collection. The system geometric factor $G_{fs}$ for the fluid pathway of the blood collection system can be determined in similar fashion as described earlier. In some embodiments, the system geometric factor $G_{fs}$, when the probe 150 may or may not be in the extended position, may be equal to or more than 7.34E+06 (1/in$^3$). In some embodiments, $G_{fs}$ may include another value. In some embodiments, the system geometric factor $G_{fs}$ may be 7.34E+06 (1/in$^3$) plus or minus 10 percent, plus or minus 25 percent, plus or minus 50 percent, or plus or minus 75 percent. In some embodiments, $G_{fs}$ may include another value, which may be selected based on a gauge and/or length of the catheter.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. An extension set comprising:

a distal connector configured to connect the extension set to a vascular access device;

an extension tube attached to and extending from a proximal portion of the distal connector, a fluid pathway being formed through the distal connector and the extension tube;

a probe having a proximal end and a distal end; and a handle that slides along the extension tube to cause the distal end of the probe to be extended from a position initially within the distal connector to a position distally from the distal connector, wherein the proximal end of the probe is secured to the proximal portion of the distal connector such that the proximal end of the probe does not move with respect to the distal connector when the distal end of the probe is extended, wherein the handle defines a channel therein, and wherein the probe is looped through the channel.

2. The extension set of claim 1, further comprising:

a sleeve that extends between the distal connector and the handle, the probe being contained within the sleeve.

3. The extension set of claim 2, further comprising:

one or more rails positioned within the sleeve, the one or more rails extending proximally from the distal connector.

4. The extension set of claim 2, wherein the sleeve compresses as the handle slides towards the distal connector.

5. The extension set of claim 1, wherein the handle surrounds the extension tube.

6. The extension set of claim 1, further comprising:

a proximal connector that is coupled to the extension tube opposite the distal connector, the fluid pathway extending through the proximal connector.

7. The extension tube of claim 1, further comprising:

an integrated device that is coupled to the extension tube opposite the distal connector, the fluid pathway extending into the integrated device.

8. The extension tube of claim 7, wherein the integrated device is a vacuum tube receiver.

9. The extension tube of claim 1, wherein the probe includes a fluid permeable distal portion.

10. The extension tube of claim 9, wherein the fluid permeable distal portion comprises a coil surrounding the probe.

11. The extension set of claim 10, wherein the coil has a distal portion that extends distally beyond the distal end of the probe.

12. The extension set of claim 1, wherein the distal end of the probe comprises a sensor.

13. The extension set of claim 1, wherein the distal connector includes one or more seals, the probe extending through the one or more seals.

14. The extension set of claim 13, wherein the one or more seals comprise a primary seal and a secondary seal positioned proximal to the primary seal, the secondary seal having a distally-facing pocket.

15. An extension set comprising:

a distal connector configured to connect the extension set to a vascular access device;

a proximal connector;

an extension tube extending between the distal connector and the proximal connector, a fluid pathway being formed through the distal connector, the extension tube and the proximal connector;

a handle that is positioned between the distal connector and the proximal connector, the handle being configured to slide along the extension tube;

a sleeve that extends between the distal connector and the handle; and a probe that is interfaced with the handle such that a proximal end of the probe is attached to a proximal portion of the distal connector and a distal end of the probe is extendable from a position initially within the distal connector to a position distally from the distal connector when the handle slides towards the distal connector, wherein the proximal end of the probe does not move with respect to the distal connector when the distal end of the probe is extended.

16. The extension set of claim 15, wherein the handle defines a channel therein, and wherein the probe is routed through the channel in the handle.

17. The extension set of claim 16, wherein the sleeve surrounds the extension tube and a portion of the probe that is positioned between the distal connector and the handle.

18. The extension set of claim 15, wherein the probe includes a coil that forms a fluid permeable distal portion of the probe.

19. A method for collecting blood comprising:

attaching an extension set to a vascular access device that is inserted into a patient's vasculature, the extension set comprising:

a distal connector by which the extension set is attached to the vascular access device;

an extension tube coupled to the distal connector;

a vacuum tube receiver coupled to the extension tube opposite the distal connector, a fluid pathway being formed through the distal connector, the extension tube and the vacuum tube receiver;

a probe having a proximal end attached to a proximal portion of the distal connector and a distal end; and a handle that slides along the extension tube to cause the distal end of the probe to be extended from a position initially within the distal connector to a position distally from the distal connector;

inserting a vacuum tube into the vacuum tube receiver; and moving the handle towards the distal connector to cause the distal end of the probe to be extended through the vascular access device and into the patient's vasculature thereby removing an occlusion that is preventing blood from flowing through the fluid pathway into the vacuum tube.

* * * * *